United States Patent [19]
Johnson

[11] 3,941,827
[45] Mar. 2, 1976

[54] PREPARATION OF HALOGENATED NITRILES

[75] Inventor: Robert Phillip Johnson, Alma, Mich.

[73] Assignee: Michigan Chemical Corporation, Chicago, Ill.

[22] Filed: Feb. 4, 1974

[21] Appl. No.: 439,470

[52] U.S. Cl. .......... 260/465.7; 260/464; 260/465 G
[51] Int. Cl.² ...................................... C07C 120/04
[58] Field of Search ............... 260/465.7, 465 G, 464

[56] References Cited
UNITED STATES PATENTS

| | | | |
|---|---|---|---|
| 2,415,261 | 2/1947 | Rogers | 260/465.7 X |
| 2,800,497 | 7/1957 | Indest | 260/465.7 |
| 3,725,458 | 4/1973 | Starks | 260/465.3 X |

OTHER PUBLICATIONS
Starks, J.A.C.S., 93, 1971, pp. 195–199.

Allen, Organic Synthesis, Collective Volume I, 2nd ed., 1941, pp. 156–157.

*Primary Examiner*—Joseph P. Brust
*Attorney, Agent, or Firm*—Robert M. Phipps; Robert S. Frieman

[57] ABSTRACT

A process is disclosed for preparing halogenated hydrocarbyl nitriles comprising reacting a metal or ammonium cyanide with a dihalogenated aliphatic or alicyclic hydrocarbon of the formula $$X-R-CH_2-X_1$$

where X and $X_1$ are chloro, bromo or iodo and R is a divalent aliphatic, alicyclic or aralkyl hydrocarbon group, in an aqueous medium in the presence of a phase transfer catalyst.

13 Claims, No Drawings

PREPARATION OF HALOGENATED NITRILES

BACKGROUND OF THE INVENTION

The present invention relates to a process for preparing halogenated aliphatic, alicyclic or aralkyl hydrocarbyl nitriles, such as 4-chlorobutyronitrile, by reacting a metal or ammonium cyanide with a dihalogenated aliphatic, alicyclic or aralkyl hydrocarbyl compound in the presence of water and a phase transfer catalyst such as a quaternary ammonium or phosphonium salt.

Haloalkyl nitriles have customarily been prepared by reacting dihaloalkanes with a metallic cyanide in a medium capable of solvating both reactants in the same phase. One medium extensively used has been a 50—50 ethanol-water mixture. The ethanol places the dihalide in solution, and the water dissolves the metal cyanide. The use of ethanol in the reaction system requires that precautions be taken during the reaction to avoid the danger of fire. The yield of the desired halohydrocarbyl nitrile prepared by the above method is usually in the range of 55 to 75 percent based upon the dihaloalkane reactant. One of the principal side reactions which reduces the yield of the product is the formation of the dinitrile. If a method for preparing halohydrocarbyl nitriles could be devised which could eliminate the need for an organic solvent while simultaneously improving the yield of the halohydrocarbyl nitrile product, it would represent an important advance in the art. Providing such a process constitutes one of the principal objects of this invention.

SUMMARY OF THE INVENTION

The present invention pertains to a process for preparing a halogenated aliphatic, alicyclic or aralkyl hydrocarbyl nitrile comprising reacting a metal or ammonium cyanide with a dihalogenated aliphatic alicyclic or aralkyl hydrocarbon of the formula $$X—R—CH_2—X_1$$

where X and $X_1$ are chloro, bromo or iodo and R is a divalent aliphatic, alicyclic or aralkyl hydrocarbon group, in an aqueous medium in the presence of a phase transfer catalyst.

The cyanide reactant is a metal or ammonium cyanide. Preferred metals because of their low cost and ability to ionize readily in water are the alkali metals such as sodium and potassium. The alkaline earth metals, magnesium, calcium, strontium, barium and the like are also useful herein as are the other metals of Groups 3 to 8 of the Periodic Table of the Elements. The ammonium group can be either the unsubstituted $NH_4+$ group, or a substituted ammonium group such as a quaternary ammonium group. Also included within the scope of the invention are those ammonium groups where one, two or three of the hydrogen atoms are displaced by a hydrocarbon group. Examples include methylammonium, dibenzylammonium, butyldibenzylammonium, methyldiethylammonium, diethylammonium, benzylammonium and the like.

The dihalogenated hydrocarbon has the formula $$X—R—CH_2—X_1$$

where X and $X_1$ are chloro, bromo or iodo, and R is a divalent aliphatic, alicyclic or aralkyl hydrocarbon group.

The two X groups can be the same or different halogen groups. One class of preferred compounds are those where X is a chloro group and $X_1$ is a bromo group. Other combinations of X and $X_1$ groups include chlorine and chlorine, bromine and bromine, iodine and iodine, chlorine and iodine, bromine and chlorine, iodine and bromine, iodine and chlorine, and bromine and iodine.

The R group can be any divalent aliphatic or alicyclic hydrocarbon group such as alkylene, alkenylene, alkynylene, cycloalkylene and the like. Another group represented by R is an aralkyl group where the alkyl and aryl portions are arranged in the dihalogenated hydrocarbon in the following manner:

$$X—alkyl-aryl—CH_2—X_1.$$

Hence the halogen atom must be attached to the alkyl portion of the aralkyl group and not to the aromatic moiety. Examples of suitable aralkyl groups useful herein include tolylene, i.e., —$CH_2C_6H_4$—; ethylphenylene, i.e., —$C_2H_4C_6H_4$—; and the like. The R group can be of any size up to 20 or more carbon atoms, but preferably has a maximum of about eight carbon atoms and more preferably about four carbon atoms. Preferred R groups are the alkylene, alkenylene and cycloalkylene groups, and more preferably the alkylene groups having a maximum of about four carbon atoms. Examples of suitable R groups include trimethylene, 1-methylpropylene, dimethylene, vinylene, allylene, cyclohexylene and the like.

Examples of dihalohydrocarbons useful in the practice of this invention include 1-chloro-3-bromopropane, 1,3-dichloropropane, 1,4-dichlorobutane, 1,3-dichlorobutane, 1-chloro-3-bromopropene-1, 1-bromomethyl-4-chlorocyclohexane, $\alpha,\alpha'$-dibromo-p-xylene, $\alpha$-bromo-$\alpha'$-chloro-p-xylene 4-(2-bromoethyl)-toluene, 1-chloro-4-iodobutene-2, 1-iodo-2-chloroethane, 1-bromo-2-chloroethane, 1,2-dibromobutane, 1-iodo-4-bromobutene-1, 1-chloro-3-bromopropene, and 1-chloro-3-bromooctadecane. Of the foregoing, the $\alpha,\omega$-dihaloalkanes are the most preferred reactants for use in the practice of the present invention. The preparation of $\omega$-haloalkyl nitriles from the $\alpha,\omega$-dihaloalkanes in good yield is an exceptionally unexpected feature of this invention since one skilled in the art would expect the reaction of a dihaloalkane with a cyanide to produce a large amount of the dinitrile at the expense of the desired mono-halo-mononitrile product.

The reaction is conducted in an aqueous medium. Because of the simplicity and availability of water, it is preferable that water be the sole solvent and dispersing medium for the reactants. For certain variations, it may be desirable to use other liquids as co-dispersants such as benzene, chloroform, cyclohexane and the like.

The phase transfer catalyst is an essential component required in the practice of the present invention. The concept of phase transfer catalysis has been reported in the literature for a number of reactions, and a large number of catalytic compounds known to be useful for the production of alkyl nitriles can be used herein. Examples include quaternary ammonium, phosphonium and arsonium salts, such as tetramethylammonium chloride, cetyltrimethylammonium bromide, benzyltrimethylammonium bromide, tricaprylylmethylammonium chloride, benzyltriethylammonium chloride, dibenzyldiethylammonium nitrate, diethyldipropylammonium sulfate, dihexyldimethylammonium iodide, tetrabutylammonium hydrogen sulfate, tetrabutylphosphonium bromide, tetraethylphosphonium chloride, ethyltribenzylphosphonium fluoride, cetyltrimethylphosphonium acetate, tricaprylylethylphosphonium nitrate, tributylhexadecylphosphonium bromide, tetrabutylphosphonium bromide and diethyldibenzylarsonium nitrate.

The amount of phase transfer catalyst which can be used can vary from a small amount such as 0.01 mole or less per mole of the dihalide reactant up to am amount exceeding the stoichiometric amount required to displace the $X_1$ halogen component of the dihalide reactant. The amount of catalyst preferably used because of economic considerations is from about 0.01 to 0.5, and more preferably from about 0.02 to about 0.15, mole per mole of dihalide reactant. If the cyanide reactant is wholly or partially a quaternary ammonium cyanide, the amount of phase transfer catalyst can be reduced or even eliminated, depending upon the equivalent weight of the quaternary ammonium ion present.

The conditions under which the reaction of the above reactants can be conducted can vary depending upon the reactants employed. Reaction temperatures can be from the freezing point of the aqueous medium to a temperature greater than the boiling point of the medium. Since reaction pressures can be either superatmospheric or subatmospheric, the reaction temperatures can be substantially higher than 100°C or even lower than 0°C. Careful selection of reaction temperatures and pressures can minimize the formation of undesirable by-products, and such selection of optimum reaction temperatures, pressures and other operating conditions therefore constitutes a preferred embodiment of this invention. Preferred reaction temperatures for dihaloalkanes and alkali metal cyanides range from about 40° to about 110°C, and more preferably from about 50° to about 100°C. For 1-chloro-3-bromopropane and sodium cyanide reactants, a reaction temperature of from about 65° to about 85°C is particularly preferred. Reaction pressures are most conveniently maintained at atmospheric pressure, but pressures from 0.1 or less up to 10 or more atmospheres are included within the scope of this invention.

Another variable which has an effect upon the production of the dinitrile by-product is the molar ratio of the dihalide reactant to the cyanide reactant. Even though molar ratios of dihalide to cyanide of less than 1 to 1, such as 0.7 or 0.8 moles of dihalide to one mole of cyanide, are within the scope of this invention, molar ratios of dihalide to cyanide of at least 1 to 1, more preferably at least 1.5 to 1, and even more preferably at least 2 to 1, are particularly useful since the production of the dinitrile is minimized, thereby facilitating the recovery and purification of the desired halohydrocarbyl nitrile product.

One reaction technique which has been found to be capable of reducing the formation of the dinitrile has been the gradual addition of the cyanide to the reaction medium containing the dihalide. Instead of adding the cyanide in one step, the cyanide addition can be made in a number of steps, or even continuously during the entire reaction period. If the production of the halohydrocarbyl nitrile is carried out in a continuous reaction, both the dihalide and the cyanide can be added continuously or intermittently in such a manner that the molar ratio of dihalide to cyanide is always greater than 2 to 1, and preferably much greater, on the order of 5 to 1 or even 10 to 1.

One technique which can be employed to reduce the formation of the undesirable by-products is the application of a vacuum when the halohydrocarbyl nitrile is being removed from the system by distillation. Without some reduction in pressure, the temperatures necessary for distillation of many of the halonitriles within the scope of this invention are so high that product decomposition occurs. Reduced pressures during product distillation, on the order of 0.5 to 250 mm.Hg, have been beneficially employed in the process of this invention.

In one preferred embodiment of this invention, an alkali metal cyanide is reacted with a dihaloalkane where the two halogen atoms on the alkane are different. Chlorine and bromine are examples of different halogen atoms which are commonly used in combination with each other to form chloro-bromoalkanes. When the chloro-bromoalkane is 1-chloro-3-bromopropane, the principal reaction product will be 4-chlorobutyronitrile. Another reaction product which will also be formed, however, is 4-bromobutyronitrile. If it is desirable to minimize the formation of the bromonitrile, the reaction system containing the haloalkyl nitrile can be washed with some metal chloride such as sodium chloride prior to the distillation step.

Temperature control, already described as important in controlling the formation of the dinitrile, is also important in controlling the ratio of chloro-to bromoalkyl nitriles. In general, the formation of a high proportion of the chloroalkyl nitrile can be attained by conducting the reaction at a temperature below 100°C.

If the X halogen atom is attached to a carbon atom in the R group which is not a —$CH_2$— group, the replacement of the X halogen atom instead of the $X_1$ halogen atom with a cyanide group can be minimized. If for instance the dihalide reactant is 2-chloropropyl bromide, the chlorine atom is less available for reaction with the cyanide compound than is the bromine atom, and chlorohydrocarbyl cyanide with a high degree of purity is thereby formed.

The halohydrocarbyl nitriles produced by the process of this invention are useful intermediates in the synthesis of pharmaceuticals, photographic chemicals and polymers. Specifically, 4-halobutyronitriles can be used as reactants in the manufacture of lysine, an amino acid useful for medicinal and nutritional purposes. The halohydrocarbyl nitriles as a generic class are also useful as reactants in organic syntheses for introducing hydrocarbyl cyanide groups into compounds, thereby making such compounds useful in the preparation of biologically active materials. In addition, 4-halobutyronitriles can be employed as reactants in the manufacture of herbicidal chemicals taught in U.S. Pat. No. 3,546,295. Other halohydrocarbyl nitriles can be employed in organic manufacture as alkylating agents for the introduction of cyanohydrocarbyl groups. Thus, for example, the use of 3-bromopropionitrile for the commercially significant cyanoethylation reaction of several compounds has been detailed by R. F. Butskus in J. Gen. Chem., U.S.S.R., 30, 1799 (1960). The antifibrinolytic drug e-amino-caproic acid can be prepared from 6-chloro-capronitrile by a variation of the procedure in Organic Syntheses, Collective Volume II, 25 (1943).

EXAMPLE 1

To 315 grams (2 moles) of 1-chloro-3-bromopropane was added 49 grams (1 mole) of sodium cyanide, 25 ml. of water, and 18.2 grams of cetyltrimethylammonium bromide. The mixture was heated with stirring to 100°C as a reaction exotherm occurred. Stirring of the reaction mixture was continued during the remainder of the 5.5 hour period, after which time the reaction mixture was fractionally distilled under reduced pressure. The combined yield of chloro- and bromobutyronitrile was 74%, based upon vapor-phase chromatographic analysis.

EXAMPLE 2

The procedure of Example 1 was repeated except that the temperature was maintained at 95°C for a 10 hour period. VPC analysis showed the yield of the chloro-and bromobutyronitrile to be 71%.

EXAMPLE 3

Example 1 was repeated except that the molar ratio of chlorobromopropane to the cyanide was adjusted to 1.6 to 1 instead of 2 to 1. Secondly, the reaction temperature was held at 75 to 80°C for the first hour and at about 70°C for an additional two hours, instead of using the reaction conditions of Example 1. Thirdly, after the reaction was terminated, the organic layer was separated from the aqueous layer and washed with 175 grams of sodium chloride in 300 ml. of water. The yield of the chloro-and bromobutyronitrile was 72% based upon VPC analysis. Percent glutaronitrile was 7.1%.

EXAMPLE 4

The procedure of Example 1 was repeated except that the molar ratio of the chlorobromopropane to the cyanide was adjusted to 1.1 to 1 instead of 2 to 1. In addition, the reaction temperature was maintained at 75° to 80°C for 2.5 hours, during which time the cyanide was added gradually instead of all at once at the onset of the reaction. After the 2.5 hour period, the reaction temperature was maintained at 75° to 80°C for an additional hour, during which time no further cyanide was added. The yield of chloro-and bromobutyronitrile based upon VPC analysis was 82%; yield of glutaronitrile was 9.6%.

EXAMPLE 5

The procedure of Example 1 was followed except that a reaction temperature of 70° to 75°C was utilized with the cyanide reactant being added to the reaction mixture over a 2 hour period. Following the cyanide addition, the reaction mixture was maintained at the 70 to 75°C temperature for an additional 2 hours. The yield of chloro and bromobutyronitrile based upon VPC analysis was 90%; yield of glutaronitrile was 1.1%.

Comparison of the first four examples with Example 5 shows that the process variables described hereinabove can be adjusted to increase appreciably the yield of the desired halobutyronitrile while simultaneously reducing the formation of undesirable by-products such as glutaronitrile.

EXAMPLE 6

The following Example is presented to illustrate other embodiments which can be practiced utilizing the foregoing examples as background information.

Two moles of $\alpha$-bromo-$\alpha'$-chloro-p-xylene is added to a solution containing 0.25 mole of potassium cyanide and 0.05 mole of tetrabutylphosphonium bromide in 25 ml. of water. The mixture is heated wtih stirring to 75°C at which time an additional 0.75 mole of potassium cyanide dissolved in 25 ml. of water is added dropwise over a 2 hour period. During the 2 hour period care is taken to maintain the reaction temperature at 75° to 80°C. After the cyanide addition is complete, the reaction mixture is maintained at 75° to 80°C for an additional 30 minutes, after which time the desired $\alpha$-chloro-p-toluyl nitrile is removed by distillation under reduced pressure.

What is claimed is:

1. A process for preparing 4-halobutyronitrile wherein said nitrile is 4-chlorobutyronitrile, 4-bromobutyronitrile or mixtures thereof comprising reacting a water ionizable metal or ammonium cyanide with 1-chloro-3-bromopropane, in a molar ratio of 1-chloro-3-bromopropane to cyanide of about 1:1 to about 2:1, the reaction medium being water, and in the presence of a phase transfer catalyst, the reaction temperature being maintained at about 50° to about 100°C.

2. A process according to claim 1 wherein said metal or ammonium cyanide is an alkali metal cyanide.

3. A process according to claim 2 wherein said alkali metal cyanide is sodium cyanide.

4. A process according to claim 1 wherein said phase transfer catalyst is a quaternary ammonium or phosphonium compound.

5. A process according to claim 1 wherein said phase transfer catalyst is a quaternary ammonium halide.

6. A process according to claim 5 wherein said quaternary ammonium halide is cetyltrimethyl ammonium bromide.

7. A process according to claim 1 wherein said reaction temperature is from about 65° to about 85° C.

8. A process according to claim 7 wherein said reaction temperature is from about 70° to about 75° C.

9. A process according to claim 8 wherein said molar ratio is from about 1.5:1 to about 2:1.

10. A process according to claim 9 wherein said molar ratio is 1.5:1.

11. A process according to claim 9 wherein said molar ratio is 2:1.

12. A process according to claim 1 wherein the aqueous layer of the reaction mixture is washed with a metal chloride solution prior to removal of said 4-halobutyronitrile.

13. A process for preparing 4-halobutyronitrile wherein said nitrile is selected from the group consisting of 4-chlorobutyronitrile, 4-bromobutyronitrile or mixtures thereof comprising reacting an alkali metal cyanide with 1-chloro-3-bromopropane in a molar ratio of about 1:5 to 2:1, the reaction medium being water, in the presence of a quaternary ammonium halide phase transfer catalyst having at least 10 carbon atoms, the reaction temperature being maintained at about 50° to 100°C.

* * * * *